United States Patent [19]

Valsecchi et al.

[11] Patent Number: 6,011,166

[45] Date of Patent: *Jan. 4, 2000

[54] TRINUCLEAR CATIONIC PLATINUM COMPLEXES HAVING ANTITUMOR ACTIVITY AND PHARMACEUTIAL COMPOSITIONS CONTAINING THEM

[75] Inventors: Mariella Valsecchi; Paolo Pavesi; Carlo Bugatti; Ernesto Menta; Fernando Giuliani; Carla Manzotti; Silvano Spinelli, all of Monza, Italy; Nicholas Farrell, Richmond, Va.

[73] Assignee: F. Hoffmann-La Roche AG, Basel, Switzerland

[*] Notice: This patent issued on a continued prosecution application filed under 37 CFR 1.53(d), and is subject to the twenty year patent term provisions of 35 U.S.C. 154(a)(2).

[21] Appl. No.: 08/836,667

[22] PCT Filed: Nov. 13, 1995

[86] PCT No.: PCT/EP95/04455

§ 371 Date: Jul. 25, 1997

§ 102(e) Date: Jul. 25, 1997

[87] PCT Pub. No.: WO96/16068

PCT Pub. Date: May 30, 1996

[30] Foreign Application Priority Data

Nov. 24, 1994 [IT] Italy .................................. MI94A2383

[51] Int. Cl.[7] ....................................................... C07F 15/00
[52] U.S. Cl. ............................................ 556/137; 556/136
[58] Field of Search ............................ 556/137; 568/137, 568/136

[56] References Cited

U.S. PATENT DOCUMENTS 5,380,897   1/1995   Hoeschele ................................ 556/137

OTHER PUBLICATIONS

International Publication No. WO 95/26968, published Oct. 12, 1995.

*Primary Examiner*—Gary Geist
*Assistant Examiner*—Jean F. Vollano
*Attorney, Agent, or Firm*—Nikaido Marmelstein Murray & Oram, LLP.

[57] ABSTRACT

The present invention relates to trinuclear cationic platinum complexes with alkylene diamine groups connecting the three platinum moieties. The invention also relates to the antitumor activity of these complexes as well as the processes for the preparation thereof and pharmaceutical compositions containing them.

10 Claims, No Drawings

TRINUCLEAR CATIONIC PLATINUM COMPLEXES HAVING ANTITUMOR ACTIVITY AND PHARMACEUTIAL COMPOSITIONS CONTAINING THEM

This application is the national phase of PCT/EP95/04455 filed Nov. 13, 1995.

The present invention relates to platinum complexes having antitumour activity, processes for the preparation thereof and pharmaceutical compositions containing them.

TECHNOLOGICAL BACKGROUND

The use of platinum complexes such as cisplatin and carboplatin in cancer chemotherapy is well established in the art. A number of platinum complexes, such as cisplatin, are used to treat testicular, ovarian, head and neck and small-cell lung carcinomas. However, treatment with cisplatin may result in severe nephrotoxicity. A further clinical disadvantage is the problem of acquired drug resistance resulting in the tumour becoming refractory to treatment by the agent.

It is generally believed that platinum complexes such as cisplatin manifest their biological activity through covalent interaction with DNA. In particular, cisplatin induces the formation of a range of adducts on DNA including monodentate adducts, bidentate adducts, such as GG or AG and GNG intrastrand crosslinks [Reedijk et al., Structure and Bonding, (1987) 67, 53–89]. To a lesser extent, cisplatin also results in interstrand GG crosslinks and DNA-protein crosslinks [Rahmouni et al., Biochemistry, (1987) 26, 7229–7234]. These DNA lesions result in conformational changes which are reflected in bending and local unwinding of the DNA. These DNA lesions have been reported to inhibit the activity of various DNA polymerases [Vallan et al., Nucl. Acids Res., (1988) 16, 4407–4418; Pinto et al., Proc. Natl. Acad. Sci., (1985) 82, 4616–4619; Gralla et al., Cancer Res., (1987) 47, 5092–5096].

The interstrand crosslinks between two neighbouring guanine bases have also been shown to inhibit RNA polymerase function [Lemaire et al., Proc. Natl. Acad. Sci., (1991) 88, 1982–1985]. Accordingly, the cytotoxic effects of cisplatin are most likely attributable to the combined effects of these DNA lesions, rather than the result of any one specific lesion event.

Mono(platinum) and bis(platinum) complexes respectively containing one or two platinum atoms are known in the art (U.S. Pat. Nos. 4,225,529, 4,250,189, 4,533,502, 4565,884, 4,571,335 and 4,797,393). For example, mono(platinum) complexes include monomeric chloramine square-planar Pt(II) compounds which are four coordinate. The relative number of chloride and ammonia groups in such compounds may vary and these compounds may therefore be described by the general formula:

$$[PtCl_m(NH_3)_{4-m}]^{(2-m)+}$$

Thus, the structure of these compounds may vary from $[Pt(NH_3)_4]^{2+}$ where m=0 to $PtCl_4^{2-}$ where m=4. Since Cl is more substitution labile in comparison to ammonia, the complexes $[PtCl_2(NH_3)_2]$ and $[PtCl(NH_3)_3]Cl$ are considered bifunctional and monofunctional, respectively, wherein the "bis" and "mono" prefixes refers to the number of leaving ligands. The charge of the complexes is obtained by considering that the Pt(II) cation has a formal charge of +2 and thus requires a negative charge of −2 for charge neutralization. For example, when m=0, neutralization is provided by the presence of two chloride anions outside the coordination sphere.

The formation of the bond between platinum and ammonia, which is a neutral ligand, may be described as electron-pair donation from $NH_3$ to the empty orbitals on the Pt(II) atom. Thus, no electron sharing between the Pt and $NH_3$ group takes place. Because of this absence of electron sharing, the number of neutral ligands does not affect the overall charge in the Pt coordination sphere. Thus $[Pt(NH_3)_4]^{2+}$ is formally a 2+ cation requiring non-co-ordinating anion or anions, or counter-ions, having a net negative charge of 2− for neutralization of the complex. For example, neutralization can be provided by two mononegatively charged anions (e.g., $NO_3^+$, $Cl^-$, $PF_6^-$, $BF_4^-$ and monocarboxylates having the general formula $RCOO^-$) or a single dinegatively charged anion (e.g., $SO_4^{2-}$, dicarboxylates having the general formula $[R(COO)_2]^{2-}$). Therefore, for the same principles, $[PtCl_2(NH_3)_2]$ is a neutral complex.

These consideration can be applied not only to ammonia, but to neutral ligands such as primary or secondary amines as well.

It is noted that anionic ligands such as $Cl^-$ may be either co-ordinately bound (i.e., forming a Pt—Cl bond) or may act as a counter-anion without any need for covalent bond formation. The exact form that anions such as $Cl^-$ are comprised in a given platinum complex depends both on theoretical considerations (kinetic vs. thermodynamic effects) and the actual synthetic procedures utilised to make the complex (e.g., the extent of reaction, acidity, concentration of the particular anion, such as the concentration of $Cl^-$ which is contained in the reaction mixture. These considerations are applicable to other anionic and neutral ligands as well.

The fact that the overall charge of monoplatinum complexes depends on the relative number of neutral and anionic ligands which are bound to the Pt(II) metal is equally applicable for polynuclear complexes (which contain more than one Pt(II) coordinate spheres), and for Pt(IV) containing complexes wherein the oxidation state of the platinum moiety is 4+. For example, dinuclear complexes where two equivalent Pt(II) coordination spheres are linked by a diamine bridging agent may be represented by the general formula

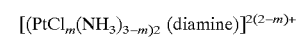

Thus, when m=2 and two bifunctional coordination spheres are present, the compound is neutral. In contrast, when m=1, only monofunctional coordination spheres are present and the platinum moiety has a formal charge of 2+ which must be counterbalanced by one or more counter-anions having a net charge of 2−.

Examples of trinuclear platinum complexes (also named tri-platinum complexes) were recently reported in literature [Yun Qu et al., Inorg. Chem., 32, 2591–2593 (1993)]. Said compounds, in which the ligands have a cis configuration, are complexes neutral or bearing an overall charge of 2+ and they can be represented by the following general formulae:

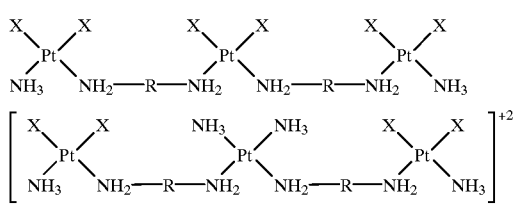

in which X means a labile ligand (such as a chlorine atom) and R means an alkylene chain. From what stated above, it is evident that, in the case of the complexes with an overall charge of 2+, said charge is located on the central platinum atom, bearing four neutral ligands, whereas the two peripheral platinum atoms are formally neutral and, as defined above, bifunctional.

DISCLOSURE OF THE INVENTION

The present invention relates to tri-platinum complexes in which the three platinum atoms are linked by diamine chains and in which the central platinum atom co-ordinates four neutral ligands, whereas the two peripheral platinum atoms both coordinate three neutral ligands and one ligand having charge −1.

Therefore, the compounds of the present invention are different from the compounds of the prior art in having an overall charge of +4 and in particular in having the central platinum atom with a formal charge of +2 and the two peripheral platinum atoms each with a formal charge of +1. Moreover, as evidenced above, the two peripheral platinum atoms are monofunctional.

Particularly, the invention relates to tri-platinum complexes of formula (I):

[PtCl(NH$_3$)$_2$NH$_2$—(CH$_2$)$_n$—NH$_2$Pt(NH$_3$)$_2$NH$_2$—(CH$_2$)$_n$—NH$_2$PtCl(NH$_3$)$_2$]$^{4+}$0.4/mz$^{-m}$ (I)

wherein n is an integer from 2 to 7;

$Z^{31\ m}$ is an anion selected from chloride, bromide, iodide, nitrate, sulfate (m=2);

m is the integer 1 or 2.

More particularly, the invention relates to tri-platinum complexes of formulae (Ia), (Ib), (Ic), (Id) and (Ie):

wherein n and $Z^{-m}$ are as above defined and the stereochemistry of the platinum atoms is as defined in the above formulae.

In the following description, the wording "compounds of formula (I)" will mean in general the compounds of formulae (Ia), (Ib), (Ic), (Id) and (Ie). The compounds of formula (Ia) will be described as compounds of formula (t,c,t)-[PtCl(NH$_3$)$_2$NH$_2$—(CH$_2$)$_n$—NH$_2$Pt(NH$_3$)$_2$NH$_2$—(CH$_2$)$_n$—NH$_2$PtCl(NH$_3$)$_2$]$^{4+}$0.4/mZ$^{-m}$ as well. Analogously, the compounds of formula (Ib), (Ic), (Id) and (Ie) will be described as compounds of formulae (c,c,c)—, (c,t,c)—, (c,c,t)— and (t,t,c)-[PtCl(NH$_3$)$_2$NH$_2$—(CH$_2$)$_n$—NH$_2$Pt(NH$_3$)$_2$NH$_2$—(CH$_2$)$_n$—NH$_2$PtCl(NH$_3$)$_2$]$^{4+}$0.4/mZ$^{-m}$, respectively.

Preferred compounds of formula (I) are those in which n is the integer 6.

Particularly preferred compounds of formula (I) are those in which n is the integer 6, Z-m is a chloride or nitrate anion and m is the integer 1.

The present invention also relates to the processes for the preparation of the compounds of formula (I).

A method for the preparation of the compounds of formula (Ia) (t,c,t)-[PtCl(NH$_3$)$_2$NH$_2$—(CH$_2$)$_n$—NH$_2$Pt(NH$_3$)$_2$—NH$_2$—(CH$_2$)$_n$—NH$_2$PtCl(NH$_3$)$_2$]$^{4+}$0.4/mZ$^{-m}$ is that involving the synthesis of the intermediate (III) starting from transplatin, previously activated by substitution of a chlorine atom with dimethylformamide, by reaction with an amine of formula (II), as shown in the following scheme:

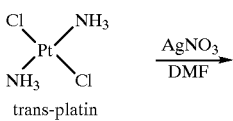
trans-platin

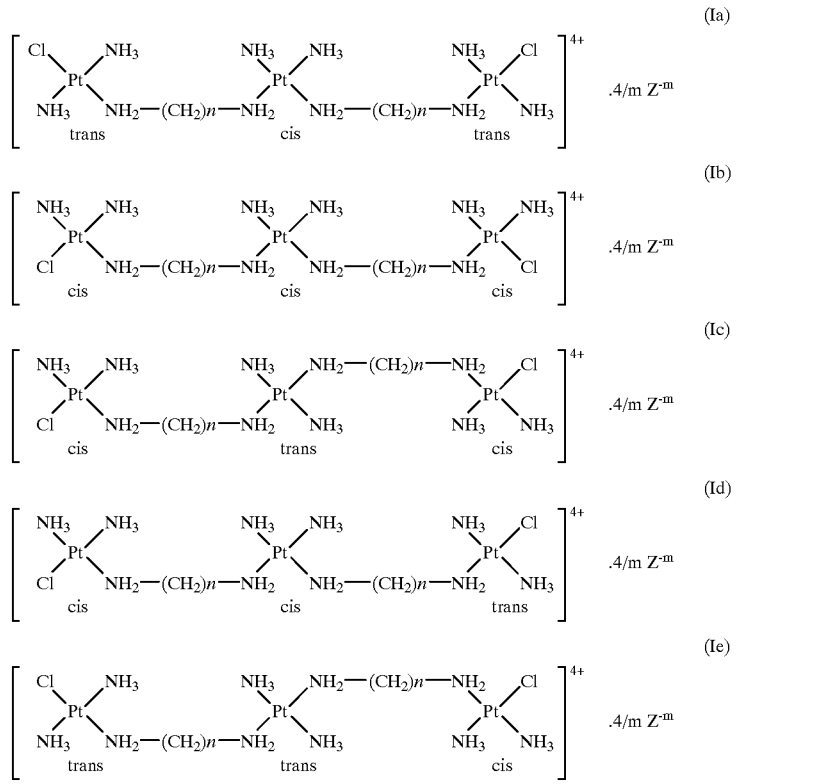

-continued

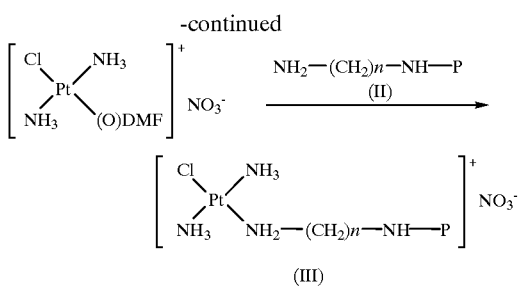

(III)

wherein P is a suitable conventional protecting group such as tert-butoxycarbonyl or p-methoxybenzyloxycarbonyl, n is as above defined. The intermediate of formula (III) yields, after cleavage of the protecting group P, the intermediate of formula (IV):

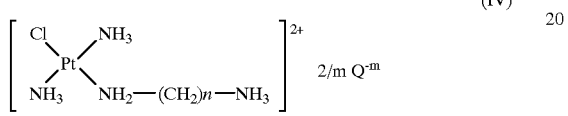

(IV)

in which n is as above defined, $Q^{-m}$ is a counter-ion which depends on the conditions of cleavage of the group P. For example, if P is a tert-butoxycarbonyl group, Q-m can be a chloride or a trifluoroacetate anion.

The intermediate (IV) is then transformed into the intermediate (V):

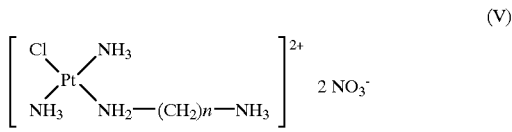

(V)

wherein n is as defined above, by means of an exchange reaction between the $Q^{-m}$ ion and the nitrate ion. Said exchange reaction, when $Q^{-m}$ is a chloride anion, can be carried out in the presence of silver nitrate and in solvents such as water or alcohols (methanol, ethanol). The intermediate (V) is then reacted with half a mole of cisplatin, previously activated by substitution of both the chlorine atoms with two molecules of dimethylformamide, to give the compounds of formula (Ia):

in which $Z^{-m}$ is a nitrate anion.

Analogously, the compounds of formula (Ib) can be prepared by substituting trans-platin with cisplatin in the first synthesis step, obtaining the intermediate of formula (IIIb):

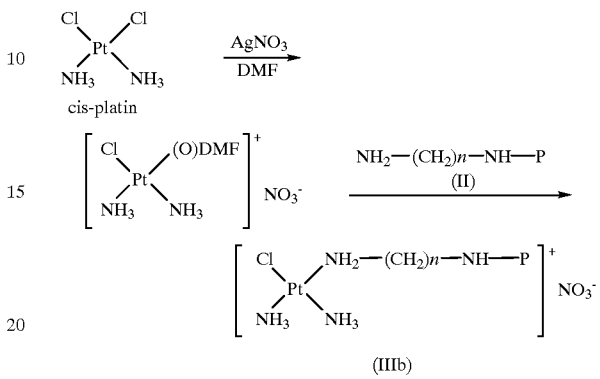

(IIIb)

which can be reacted, as previously described, according to the following synthesis steps:

i) cleavage of the protecting group P;

ii) exchange reaction of $Q^{-m}$ anion with a nitrate anion;

iii) reaction of the intermediate obtained in step ii) with half a mole of cisplatin, previously activated with two molecules of dimethylformamide.

The compounds of formula (Ic) can be prepared, starting from the above intermediate of formula (IIIb), according to the following synthesis steps:

i) cleavage of the protecting group P;

ii) exchange reaction of $Q^{-m}$ anion with a nitrate anion;

iii) reaction of the intermediate obtained in step ii) with half a mole of trans-platin, previously activated with two molecules of dimethylformamide.

The compounds of formula (Ie) (t,t,c)-[PtCl(NH$_3$)$_2$—NH$_2$—(CH$_2$)$_n$—NH$_2$Pt(NH$_3$)$_2$NH$_2$—(CH$_2$)$_n$—NH$_2$PtCl(NH$_3$)$_2$]$^{4+}$0.4/mZ$^{-m}$ can be prepared, starting from the intermediate (III), as depicted in the following scheme:

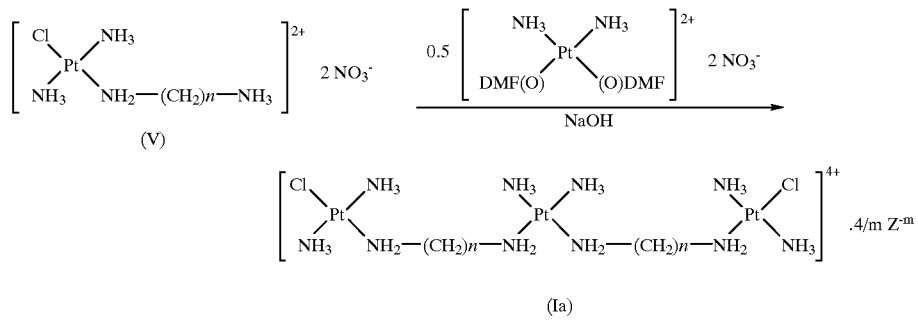

(Ia)

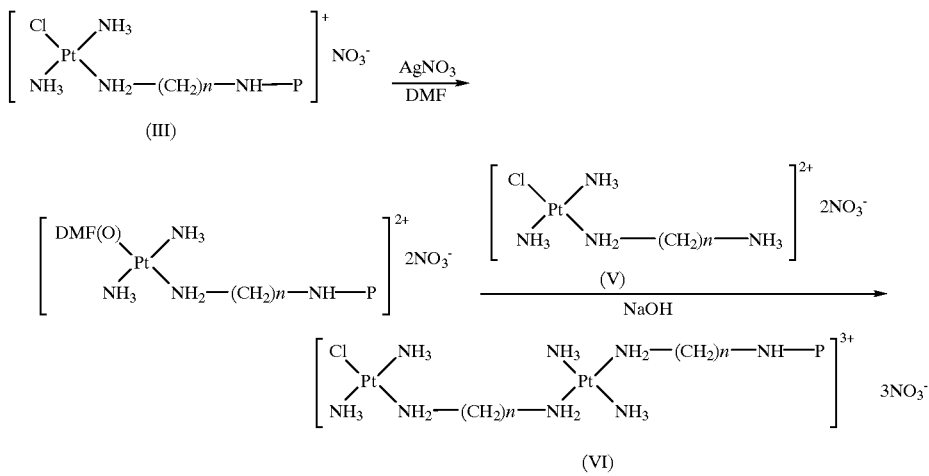

The intermediate (III), activated by substitution of the chlorine atom with a molecule of dimethylformamide, is reacted with the intermediate (V), prepared as previously described, to give the intermediate (VI), which is in its turn converted into the compounds of formula (Ie) by means of the following synthesis steps:

i) cleavage of the protecting group P;
ii) exchange reaction of $Q^{-m}$ anion with a nitrate anion;
iii) reaction of the intermediate obtained in step ii) with one mole of cisplatin, previously activated with one molecule of dimethylformamide.

Analogously, the compounds of formula (Id) (c,c,t)-[PtCl $(NH_3)_2NH_2$—$(CH_2)_n$—$NH_2Pt(NH_3)_2NH_2$—$(CH_2)_n$— $NH_2PtCl$ —$(NH_3)_2]^{4+}0.4/mZ^{-m}$ can be prepared starting from the intermediate (IIIb) following a synthesis scheme identical to that one above depicted, the only difference being the different stereochemistry of the platinum atoms:

The intermediate (VIb) is reacted according to the following synthesis steps, to give the compounds of formula (Id):

i) cleavage of the protecting group P;
ii) exchange reaction of $Q^{-m}$ anion with a nitrate anion;
iii) reaction of the intermediate obtained in step ii) with one mole of trans-platin, previously activated with one molecule of dimethylformamide.

Another method for the preparation of the compounds of formula (I) consists in synthesising an intermediate carrying on the central platinum atom two diamine chains and in reacting such intermediate, as the case may be, is with two equivalents of trans- or cis-platin mono-activated with dimethylformamide.

For example, the compounds of formula (Ia) can be obtained according to this method by reacting initially two moles of an amine of formula (II) with cisplatin, previously activated by substitution of both the chlorine atoms with two molecules of dimethylformamide, to give the intermediate of formula (VII):

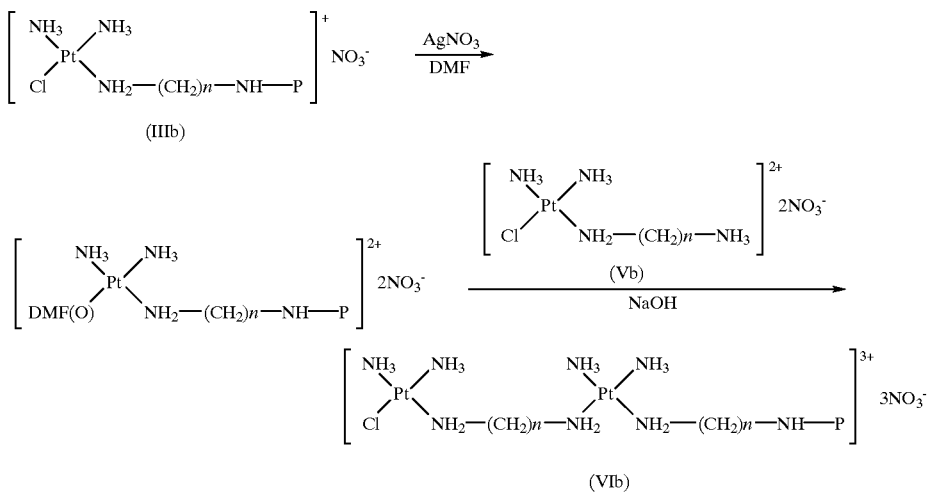

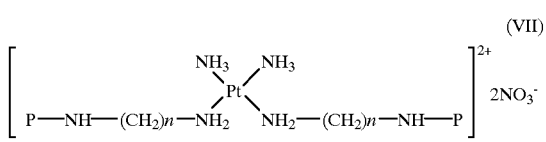

wherein P is as previously defined. By cleavage of the protecting groups P, the intermediate of formula (VIII) is obtained, in which $Q^{-m}$ is as defined above. Such intermediate is successively converted into the intermediate of formula (IX):

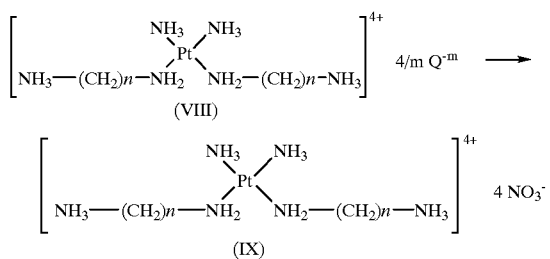

Said transformation is performed by means of an exchange reaction between $Q^{-m}$ ion and the nitrate ion.

Said exchange reaction, when $Q^{-m}$ is a chloride anion, can be carried out in the presence of silver nitrate and in solvents such as water or alcohols (methanol, ethanol).

The intermediate (IX) is then reacted with two moles of trans-platin, previously activated by substitution of a chlorine atom with dimethylformamide, to give the compounds of formula (Ia):

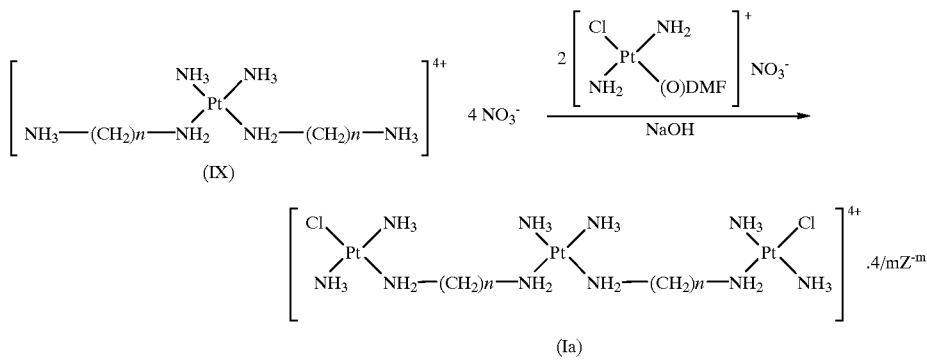

in which $Z^{-m}$ is a nitrate anion.

Analogously, by using platinum atoms with the suitable stereochemistry (trans- or cis-platin) in the various synthesis steps, are prepared all other compounds of formula (I), that is the compounds of formula (Ib), (Ic), (Id) and (Ie).

The compounds of formula (I) in which $Z^{-m}$ is a nitrate anion, prepared according to the methods described above, can then be transformed into the compounds of formula (I) in which $Z^{-m}$ is halide or sulfate by conventional exchange reactions, widely reported in literature, such as treatment with alkali or alkaline-earth metal halide or sulfate. Alternatively, compounds of formula (I) in which $Z^{-m}$ is sulfate anion can be obtained from the corresponding compounds of formula (I) with $Z^{-m}$ is halide, by treatment with silver sulfate.

Possible methods for removing the protecting groups P involve the treatment with inorganic (such as aqueous hydrochloric acid or in alcohol or ether solution) or organic acids (such as trifluoroacetic acid). When P is a tert-butoxycarbonyl group, preferred conditions for its cleavage are those which envisage the use of hydrogen chloride in alcoholic solution. In this case, as stated above, the counter-ion $Q^{-m}$ will be the chloride ion.

The compounds of the invention generally have a good solubility in water, in physiological and in water-miscible solvents.

The compounds of the invention not only have a marked antitumour activity, but also a low toxicity, therefore their therapeutical index is particularly favourable.

Moreover, the high water solubility of the triplatinum complexes of the present invention, makes the preparation of the parenteral and oral pharmaceutical forms easy.

The compounds of the invention were tested for their cytotoxic effect in vitro on various tumour cell lines, among which murine leukemia L-1210, human ovarian carcinoma A2780 or the respective sub-lines cisplatin resistant L-1210/CDDP and A2780/CDDP.

The test on the cell line A2780 is an established method for the evaluation of platinum complexes as antitumour agents. Moreover, the compounds of the invention were tested in an in vivo test in which L-1210 tumour cells are inoculated intraperitoneally in a mouse and the compound is administered intraperitoneally 24, 120 and 216 hours after inoculation of the tumour. The compounds of the invention evidenced a high antitumour effect in the above experimental models.

The platinum complexes of the invention resulted particularly active when administered in association with other platinum complexes having antitumour activity, showing a synergistic effect.

A pharmaceutical composition containing at least one compound of formula (I) in combination with a platinum complex having antitumour activity is a further object of the present invention.

The compounds of formula (I), when administered to humans and animals bearing tumours which can be treated with platinum complexes, at doses ranging from 1 mg to 1.2 g per square meter of body area, are capable of inducing the regression of said tumours.

Therefore, another object of the present invention is the use of the compounds of formula (I) for the preparation of a medicament useful for the treatment of tumours.

The effective dosage of the compounds of the invention can be determined by expert clinicians according to conventional methods. The relationship between the dosages used for animals of various species and sizes and those for humans (on the basis of mg/m² body area) is described by Freirech, E. J. et al., Quantitative Comparison of Toxicity of Anticancer Agents in Mouse, Rat, Hamster, Dog, Monkey and Man, Cancer Chemother. Rep., 50, N. 4, 219–244 (1966).

Usually, however, the patient will receive doses from 1 to 1200 mg/kg body weight of the complex, with a dosage regimen which will vary depending on various factors which are well known to the expert clinicians.

Sometimes it can prove advantageous to administer the platinum complexes of the present invention together with one or more agents which enhance the antitumour activity or relieve the undesirable side-effects of the platinum complex.

For example, the platinum complexes of the present invention can be administered together with reduced glutathione, as disclosed in GB 2174905 and U.S. Pat. No. 4,871,528.

The tumours in patients which can be treated with the platinum complexes of the present invention are those tumours known to be susceptible to the therapy with cisplatin. The complexes of the present invention are also active against some cisplatin-resistant tumours.

More generally, the compounds of the invention can be used for the treatment of the same pathological forms for which cisplatin is used. This includes the treatment of tumours, sensitisation or enhancement of radiations [Douple et al., Cisplatin Current Status and Developments, Ed. A. W. Prestayk et al., Academic Press, 125 (1980); Douple et al., Platinum Metals Res., 29, 118 (1985)] and the treatment of parasitic diseases such as African sleeping sickness [Farrell et al. Biochem. Pharmacol., 33, 961 (1984)].

The treatment regimen can suitably be varied, as it is well known to the expert clinician, according to the type of tumour to treat and the conditions of the patient.

A further object of the present invention are pharmaceutical compositions containing a therapeutically effective amount of at least one compound of formula (I) in admixture with conventional carriers and excipients.

The compounds of the invention are preferably administered as sterile aqueous solutions, optionally containing sodium chloride in suitable concentration (0.1–0.9 mg/ml). The solutions are preferably administered by the intravenous or intra-arterial routes, even though other administration forms can be used in particular cases.

The pharmaceutical compositions for the parenteral administration comprise sterile saline solutions, as defined above, or sterile powders for the extemporary preparation of the solutions, as well as oily preparations for intramuscular or intraperitoneal administrations.

Other useful pharmaceutical compositions can be syrups or similar liquid forms, as well as solid forms such as tablets, capsules and the like.

The pharmaceutical compositions according to the present invention are prepared according to known methods, such as those reported in Remington's Pharmaceutical Sciences Handbook, XVII Ed., Mack Pub., N.Y., U.S.A.

The following examples further illustrate the invention.

PREPARATION 1

N-BOC hexanediamine is prepared starting from its hydrochloric salt, which is a commercial product.

2.1 g of N-BOC hexanediamine hydrochloride are dissolved in diethyl ether (20 ml) and treated under stirring with 16 ml of 1 N aqueous solution of sodium hydroxide.

The organic phase is then washed with brine, dried over sodium sulfate and the solvent is evaporated off under reduced pressure to give N-BOC hexanediamine, free base, with a theatrical yield.

PREPARATION 2

Preparation of trans-[PtCl(NH$_3$)$_2$H$_2$N—(CH$_2$)$_6$—NH—BOC]$^+$NO$_3^-$—intermediate (III)

2 g of trans-platin are dissolved in 133 ml of anhydrous dimethylformamide (DMF) and added with 1.13 g of silver nitrate in one portion. The reaction mixture is kept under stirring shielded from light for 18 hours. After that, the precipitated silver chloride is filtered off and the clear filtrate is cooled to −20° C. and added with a solution of N-BOC-1,6-hexanediamine (1.36 g) in 40 ml of anhydrous DMF. The addition lasts about 30 minutes. The solution is kept under stirring at −20° C. for 3 hours and for one hour at room temperature. Solvent is then evaporated under reduced pressure keeping the temperature of the solution not above 40° C. and the residue is taken up into 200 ml of diethyl ether, kept under stirring for 20 minutes, then filtered. The resulting solid is dissolved in 200 ml of methanol and kept under stirring for 15 hours to precipitate any traces of trans-platin. The separated trans-platin is filtered off and the solution is treated worth active carbon (1 g), filtered again and finally the solvent is evaporated off under reduced pressure. The residue is purified by suspending it in acetone (100 ml) under stirring for 30 minutes. After filtration, 2.3 g of product are obtained.

Elementary analysis (calculated/found %):

C 24.33/24.05; H 5.57/5.64; N 12.90/12.84; Cl 6.53/6.40; Pt 35.93/36.06.

$^{195}$Pt-NMR in DMF/d7-DMF: −2433 ppm.

PREPARATION 3

Preparation of trans-[PtCl(NH$_3$)$_2$H$_2$N—(CH$_2$)$_6$—NH$_3$]$^{2+}$ 2NO$_3^-$—intermediate (V)

A solution of 1.5 g of trans-[PtCl(NH$_3$)$_2$H$_2$N—(CH$_2$)$_6$—NH—BOC]$^+$NO$_3^-$— in 150 ml of methanol is added with 21 ml of a 6.5 M solution of hydrogen chloride in ethanol. The reaction mixture is kept under stirring for 24 hours at room temperature, then the solid is filtered, washed on the filter with methanol and diethyl ether and finally dried.

The resulting solid is dissolved in 180 ml of methanol and added with a solution of silver nitrate (0.825 g) in 45 ml of methanol. The reaction mixture is kept under stirring at room temperature for 30 minutes, the silver chloride is filtered off and the clear filtrate is evaporated to dryness. The residue is taken up with acetone, kept under stirring for 15 minutes, filtered and dried, to obtain 0.925 g of product.

Elementary analysis (calculated/found %):

C 14.16/14.19; H 4.58/4.66; N 16.61/16.62; Cl 7.01/6.91; Pt 38.57/36.10.

$^{195}$Pt-NMR in DMF/d7-DMF: −2433 ppm.

PREPARATION 4

Preparation of trans-[BOC—NH—(CH$_2$)$_6$—NH$_2$—Pt(NH$_3$) $_2$H$_2$N—(CH$_2$)$_6$—NH—BOC]$^{2+}$2NO$_3^-$.

A suspension of 1.028 g of trans-platin in 35 ml of anhydrous DMF is added with 1.16 g of silver nitrate. The reaction mixture is heated to 60° C., shielding from light, for 5 hours, then the silver chloride precipitate is filtered off. After that, a solution of N-BOC-1,6-hexanediamine (1.48 g) in 5 ml of DMF is added and the resulting reaction mixture is kept at room temperature overnight. By dilution with 300 ml of diethyl ether a white solid separates, which is filtered, dissolved in methanol and filtered through a 0.2 micron filter to remove any traces of silver salts. The methanol solution is then diluted with diethyl ether. A white solid crystallises which is filtered and dried, to obtain 1.94 g of product.

Elementary analysis (calculated/found %):
C 33.63/33.44; H 6.93/7.00; N 14.26/14.30; Pt 24.83/25.06.
$^{195}$Pt-NMR in DMF/d7-DMF: −2687 ppm.

PREPARATION 5

Preparation of trans-[NH$_3$—(CH$_2$)$_6$—NH$_2$—Pt(NH$_3$)$_2$H$_2$N—(CH$_2$)$_6$—NH$_3$]$^{4+}$4Cl$^-$.

500 mg of trans-[BOC—NH—(CH$_2$)$_6$—NH$_2$—Pt(NH$_3$)$_2$H$_2$N—(CH$_2$)$_6$—NH—BOC]$^{2+}$2NO$_3^-$ are dissolved in 50 ml of methanol and added with 5 ml of a 6.5 M solution of hydrogen chloride in ethanol. The reaction mixture is kept under stirring at room temperature for 42 hours, then the solid is filtered and washed with diethyl ether, to obtain 340 ml of product.

Elementary analysis (calculated/found %):
C 23.81/23.14; H 6.66/6.73; N 13.88/13.51; Cl 23.42/22.03; Pt 32.23/31.68.
$^{195}$Pt-NMR in water: −2674 ppm.

PREPARATION 6

Preparation of cis-[BOC—NH—(CH$_2$)$_6$—NH$_2$—Pt(NH$_3$)$_2$H$_2$N—(CH$_2$)$_6$—NH—BOC]$^{2+}$2NO$_3^-$ —intermediate (VII)

A solution of cis-platin (3 g) in 100 ml of DMF, kept at room temperature, under stirring and inert gas atmosphere, is added with 3.4 g of silver nitrate. After 19 hours at room temperature, the silver chloride precipitate is filtered off by filtering it through a double microfiber filter. The yellow solution which is obtained is then kept under stirring and added with a solution of 4.54 g of N-BOC-1,6-hexanediamine in 12 ml of DMF. The resulting reddish solution, kept under stirring overnight, is treated with active carbon (1.5 g), filtered, then the solvent is evaporated off under reduced pressure. The residue (dark-yellow oil) is dissolved in 60 ml of methanol and filtered through a 0.2 micron filter. The solvent is evaporated off and the yellow oil residue is taken up with 350 ml of diethyl ether. The precipitate, filtered and dried in an oven, gives 6.94 g of product.

Elementary analysis (calculated/found %):
C 33.63/33.48; H 6.93/6.99; N 14.26/14.17; Pt 24.83/25.13.
$^{195}$Pt-NMR in d7-DMF: −2681 ppm.

PREPARATION 7

Preparation of cis-[NH$_3$—(CH$_2$)$_6$—NH$_2$—Pt(NH$_3$)$_2$H$_2$N—(CH$_2$)$_6$—NH$_3$]$^{4+}$4Cl$^-$.

A solution of cis-[BOC—NH—(CH$_2$)$_6$—NH$_2$—Pt(NH$_3$)$_2$H$_2$N—(CH$_2$)$_6$—NH—BOC]$^{2+}$2NO$_3^-$ (100 mg) in 1.5 ml of methanol, kept at room temperature and under stirring, is added with 1.39 ml of a solution 4.11 N of hydrogen chloride in ethanol. After 1 hour a white solid precipitate, which becomes more and more yellowish. After 23 hours the solid is filtered off, washed on the filter with the mother liquor, then with diethyl ether and finally dried in an oven overnight. 62 mg of product are obtained.

Elementary analysis (calculated/found %):
C 23.81/23.10; H 6.66/6.21; N 13.88/13.57; Cl 23.42/22.69; Pt 32.23/32.92.

EXAMPLE 1

Preparation of (t,c,t)-[PtCl(NH$_3$)$_2$NH$_2$—(CH$_2$)$_6$—NH$_2$Pt—(NH$_3$)$_2$NH$_2$—(CH$_2$)$_6$—NH$_2$PtCl(NH$_3$)$_2$]$^{4+}$4NO$_3^-$ and of (t,c,t)-[PtCl(NH$_3$)$_2$NH$_2$—(CH$_2$)$_6$—NH$_2$Pt(NH$_3$)$_2$NH$_2$—(CH$_2$)$_6$—NH$_2$PtCl—(NH$_3$)$_2$]$^{4+}$4Cl$^-$.

A solution of cis-platin (140 mg) in 4.6 ml of DMF, kept under stirring and in inert gas atmosphere, is added with 158 mg of silver nitrate. After 18 hours the silver chloride precipitate is filtered off and the resulting solution is added quickly dropwise with a solution of 472 mg of trans-[PtCl(NH$_3$)$_2$H$_2$N—(CH$_2$)$_6$—NH$_3$]$^{2+}$2NO3$^-$ (intermediate (V)—preparation 3) in 4.5 ml of DMF and with 1.04 ml of a solution 0.89 N of sodium hydroxide in methanol. The solution is kept under stirring overnight, then is filtered under vacuum and diluted with 30 ml of acetone. A yellowish oil separates, which is isolated by decantation from the liquid phase. The oil is then taken up with 10 ml of methanol and kept under stirring for 3 hours. After that, the pink solid which separates is filtered off, obtaining 384 mg of (t,c,t)-[PtCl(NH$_3$)$_2$NH$_2$—(CH$_2$)$_6$—NH$_2$Pt(NH$_3$)$_2$NH$_2$—(CH$_2$)$_6$—NH$_2$PtCl(NH$_3$)$_2$]$^{4+}$4NO$_3^-$.

Elementary analysis (calculated/found %):
C 11.63/11.51; H 4.07/4.08; N 15.83/15.48; Cl 5.72/5.34; Pt 47.24/46.08.
$^{195}$Pt-NMR in water: −2415 ppm; −2660 ppm.

350 mg of (t,c,t)-[PtCl(NH$_3$)$_2$NH$_2$—(CH$_2$)$_6$—NH$_2$Pt—(NH$_3$)$_2$NH$_2$—(CH$_2$)$_6$—NH$_2$PtCl(NH$_3$)$_2$]$^{4+}$4N$_3^-$ are dissolved in 175 ml of saline solution (sodium chloride 0.9%). After 1 hour at room temperature, the solution is filtered through a paper filter standing above a 0.2 micron Millex filter and the solvent is evaporated off under reduced pressure until the product begins crystallising (residual volume of about 10 ml). After 2 hours the solid is filtered off, washed on the filter with a bit of saline solution, then with methanol and diethyl ether. After drying it in an oven at 40° C. overnight, 195 mg of product are obtained.

Elementary analysis (calculated/found %):
C 12.73/12.53; H 4.45/4.49; N 12.37/12.08; Cl 18.78/18.44; Pt 51.68/50.63.
$^{195}$Pt-NMR in water: −2414 ppm; −2667 ppm.

EXAMPLE 2

Preparation of (c,t,c)-[PtCl(NH$_3$)$_2$NH$_2$—(CH$_2$)$_6$—NH$_2$Pt—(NH$_3$)$_2$NH$_2$—(CH$_2$)$_6$—NH$_2$PtCl(NH$_3$)$_2$]$^{4+}$4NO$_3^-$ 200 mg of trans-[NH$_3$—(CH$_2$)$_6$—NH$_2$—Pt(NH$_3$)$_2$H$_2$N—(CH$_2$)$_6$—NH$_3$]$^{4+}$4Cl$^-$ (preparation 5) are dissolved in 10 ml of distilled water and treated with 224 mg of silver nitrate. The resulting suspension is kept at room temperature and under stirring for 10 minutes, the silver chloride precipitate is removed by filtration. The filtrate is concentrated almost to dryness, then is diluted with acetone. A white solid separates which is filtered, washed with acetone and dried, to give 204 mg of trans-[NH$_3$—(CH$_2$)$_6$—NH$_2$—Pt(NH$_3$)$_2$H$_2$N—(CH$_2$)$_6$—NH$_3$]$^{4+}$4NO$_3^-$ 84 mg of cis-platin are dissolved in 10 ml of DMF and the resulting solution is added with 48 mg of silver nitrate:silver chloride suddenly precipitates. The suspension is kept under stirring at room temperature and shielded from light for 1 hour and 15 minutes, then is centrifuged and filtered through a 0.2 micron Millex filter. The filtrate is added with a solution of trans-[NH$_3$—(CH$_2$)$_6$—NH$_2$—Pt(NH$_3$)$_2$H$_2$N—(CH$_2$)$_6$—NH$_3$]$^{4+}$4NO$_3^-$ (100 mg) in 1 ml of DMF and with 0.14 ml of a solution 1 N of sodium hydroxide in methanol. After 2 hours under stirring, the solution is treated with active carbon, filtered and diluted with diethyl ether. A reddish oil separates, which is isolated by decantation from the mother liquor. The residue is then taken up with 5 ml of methanol and kept under stirring for 3 hours. After that, the solid which separates is filtered, obtaining 90 mg of product.
$^{195}$Pt-NMR in water: −2416 ppm; −2678 ppm.

EXAMPLE 3

According to the methods described in examples 1 or 2 and in preparations 2–7, starting from the suitable diamine, the following tri-platinum complexes are prepared:

(t,c,t)-[PtCl(NH$_3$)$_2$H$_2$N—(CH$_2$)$_5$—NH$_2$—Pt(NH$_3$)$_2$H$_2$N—(CH$_2$)$_5$—NH$_2$PtCl(NH$_3$)$_2$]$^{4+}$4NO$_3^-$ (t,c,t)-[PtCl(NH$_3$)$_2$H$_2$N—(CH$_2$)$_4$—NH$_2$—Pt(NH$_3$)$_2$H$_2$N—(CH$_2$)$_4$—NH$_2$PtCl(NH$_3$)$_2$]$^{4+}$4NO$_3^-$ (t,c,t)-[PtCl(NH$_3$)$_2$H$_2$N—(CH$_2$)$_3$—NH$_2$—Pt(NH$_3$)$_2$H$_2$N—(CH$_2$)$_3$—NH$_2$PtCl(NH$_3$)$_2$]$^{4+}$4NO$_3^-$ (t,c,t)-[PtCl(NH$_3$)$_2$H$_2$N—(CH$_2$)$_2$—NH$_2$—Pt(NH$_3$)$_2$H$_2$N—(CH$_2$)$_2$—NH$_2$PtCl(NH$_3$)$_2$]$^{4+}$4NO$_3^-$
(t,c,t)-[PtCl(NH$_3$)$_2$H$_2$N—(CH$_2$)$_7$—NH$_2$—Pt(NH$_3$)$_2$H$_2$N—(CH$_2$)$_7$—NH$_2$PtCl(NH$_3$)$_2$]$^{4+}$4NO$_3^-$
(t,c,t)-[PtCl(NH$_3$)$_2$H$_2$N—(CH$_2$)$_5$—NH$_2$—Pt(NH$_3$)$_2$H$_2$N—(CH$_2$)$_5$—NH$_2$PtCl(NH$_3$)$_2$]$^{4+}$4Cl$_3^-$
(t,c,t)-[PtCl(NH$_3$)$_2$H$_2$N—(CH$_2$)$_4$—NH$_2$—Pt(NH$_3$)$_2$H$_2$N—(CH$_2$)$_4$—NH$_2$PtCl(NH$_3$)$_2$]$^{4+}$4Cl$_3^-$
(t,c,t)-[PtCl(NH$_3$)$_2$H$_2$N—(CH$_2$)$_3$—NH$_2$—Pt(NH$_3$)$_2$H$_2$N—(CH$_2$)$_3$—NH$_2$PtCl(NH$_3$)$_2$]$^{4+}$4Cl$_3^-$
(t,c,t)-[PtCl(NH$_3$)$_2$H$_2$N—(CH$_2$)$_2$—NH$_2$—Pt(NH$_3$)$_2$H$_2$N—(CH$_2$)$_2$—NH$_2$PtCl(NH$_3$)$_2$]$^{4+}$4Cl$_3^-$
(t,c,t)-[PtCl(NH$_3$)$_2$H$_2$N—(CH$_2$)$_7$—NH$_2$—Pt(NH$_3$)$_2$H$_2$N—(CH$_2$)$_7$—NH$_2$PtCl(NH$_3$)$_2$]$^{4+}$4Cl$^-$
(c,t,c)-[PtCl(NH$_3$)$_2$H$_2$N—(CH$_2$)$_5$—NH$_2$—Pt(NH$_3$)$_2$H$_2$N—(CH$_2$)$_5$—NH$_2$PtCl(NH$_3$)$_2$]$^{4+}$4NO$_3^-$
(c,t,c)-[PtCl(NH$_3$)$_2$H$_2$N—(CH$_2$)$_4$—NH$_2$—Pt(NH$_3$)$_2$H$_2$N—(CH$_2$)$_4$—NH$_2$PtCl(NH$_3$)$_2$]$^{4+}$4NO$^-$
(c,t,c)-[PtCl(NH$_3$)$_2$H$_2$N—(CH$_2$)$_3$—NH$_2$—Pt(NH$_3$)$_2$H$_2$N—(CH$_2$)$_3$—NH$_2$PtCl(NH$_3$)$_2$]$^{4+}$4NO$_3^-$
(c,t,c)-[PtCl(NH$_3$)$_2$H$_2$N—(CH$_2$)$_2$—NH$_2$—Pt(NH$_3$)$_2$H$_2$N—(CH$_2$)$_2$—NH$_2$PtCl(NH$_3$)$_2$]$^{4+}$4NO$_3^-$
(c,t,c)-[PtCl(NH$_3$)$_2$H$_2$N—(CH$_2$)$_7$—NH$_2$—Pt(NH$_3$)$_2$H$_2$N—(CH$_2$)$_7$—NH$_2$PtCl(NH$_3$)$_2$]$^{4+}$4NO$_3^-$
(c,t,c)-[PtCl(NH$_3$)$_2$H$_2$N—(CH$_2$)$_5$—NH$_2$—Pt(NH$_3$)$_2$H$_2$N—(CH$_2$)$_5$—NH$_2$PtCl(NH$_3$)$_2$]$^{4+}$4Cl$^-$
(c,t,c)-[PtCl(NH$_3$)$_2$H$_2$N—(CH$_2$)$_4$—NH$_2$—Pt(NH$_3$)$_2$H$_2$N—(CH$_2$)$_4$—NH$_2$PtCl(NH$_3$)$_2$]$^{4+}$4Cl$^-$
(c,t,c)-[PtCl(NH$_3$)$_2$H$_2$N—(CH$_2$)$_3$—NH$_2$—Pt(NH$_3$)$_2$H$_2$N—(CH$_2$)$_3$—NH$_2$PtCl(NH$_3$)$_2$]$^{4+}$4Cl$^-$
(c,t,c)-[PtCl(NH$_3$)$_2$H$_2$N—(CH$_2$)$_2$—NH$_2$—Pt(NH$_3$)$_2$H$_2$N—(CH$_2$)$_2$—NH$_2$PtCl(NH$_3$)$_2$]$^{4+}$4Cl$^-$
(c,t,c)-[PtCl(NH$_3$)$_2$H$_2$N—(CH$_2$)$_7$—NH$_2$—Pt(NH$_3$)$_2$H$_2$N—(CH$_2$)$_7$—NH$_2$PtCl(NH$_3$)$_2$]$^{4+}$4Cl$^-$
(c,c,c)-[PtCl(NH$_3$)$_2$H$_2$N—(CH$_2$)$_5$—NH$_2$—Pt(NH$_3$)$_2$H$_2$N—(CH$_2$)$_5$—NH$_2$PtCl(NH$_3$)$_2$]$^{4+}$4NO$_3^-$
(c,c,c)-[PtCl(NH$_3$)$_2$H$_2$N—(CH$_2$)$_4$—NH$_2$—Pt(NH$_3$)$_2$H$_2$N—(CH$_2$)$_4$—NH$_2$PtCl(NH$_3$)$_2$]$^{4+}$4NO$_3^-$
(c,c,c)-[PtCl(NH$_3$)$_2$H$_2$N—(CH$_2$)$_3$—NH$_2$—Pt(NH$_3$)$_2$H$_2$N—(CH$_2$)$_3$—NH$_2$PtCl(NH$_3$)$_2$]$^{4+}$4NO$_3^-$
(c,c,c)-[PtCl(NH$_3$)$_2$H$_2$N—(CH$_2$)$_2$—NH$_2$—Pt(NH$_3$)$_2$H$_2$N—(CH$_2$)$_2$—NH$_2$PtCl(NH$_3$)$_2$]$^{4+}$4NO$_3^-$
(c,c,c)-[PtCl(NH$_3$)$_2$H$_2$N—(CH$_2$)$_7$—NH$_2$—Pt(NH$_3$)$_2$H$_2$N—(CH$_2$)$_7$—NH$_2$PtCl(NH$_3$)$_2$]$^{4+}$4NO$_3^-$
(c,c,c)-[PtCl(NH$_3$)$_2$H$_2$N—(CH$_2$)$_5$—NH$_2$—Pt(NH$_3$)$_2$H$_2$N—(CH$_2$)$_5$—NH$_2$PtCl(NH$_3$)$_2$]$^{4+}$4NO$_3^-$
(c,c,c)-[PtCl(NH$_3$)$_2$H$_2$N—(CH$_2$)$_4$—NH$_2$—Pt(NH$_3$)$_2$H$_2$N—(CH$_2$)$_4$—NH$_2$PtCl(NH$_3$)$_2$]$^{4+}$4Cl$^-$
(c,c,c)-[PtCl(NH$_3$)$_2$H$_2$N—(CH$_2$)$_3$—NH$_2$—Pt(NH$_3$)$_2$H$_2$N—(CH$_2$)$_3$—NH$_2$PtCl(NH$_3$)$_2$]$^{4+}$4Cl$^-$
(c,c,c)-[PtCl(NH$_3$)$_2$H$_2$N—(CH$_2$)$_2$—NH$_2$—Pt(NH$_3$)$_2$H$_2$N—(CH$_2$)$_2$—NH$_2$PtCl(NH$_3$)$_2$]$^{4+}$4Cl$^-$
(c,c,c)-[PtCl(NH$_3$)$_2$H$_2$N—(CH$_2$)$_7$—NH$_2$—Pt(NH$_3$)$_2$H$_2$N—(CH$_2$)$_7$—NH$_2$PtCl(NH$_3$)$_2$]$^{4+}$4Cl$^-$

We claim:

1. Tris-platinum complexes of formula (I):

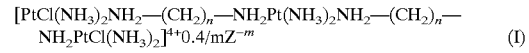

(I)

wherein n is an integer from 2 to 7;

$Z^{-m}$ is a halide selected from chloride, bromide, iodide; m=1), a nitrate anion (m=1) or a sulfate anion (m=2).

2. Complexes according to claim 1, of formula (Ia):

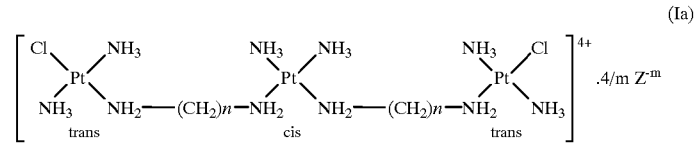

(Ia)

3. Complexes according to claim 1, of formula (Ib):

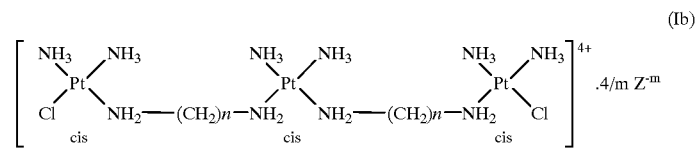

(Ib)

4. Complexes according to claim 1, of formula (Ic):

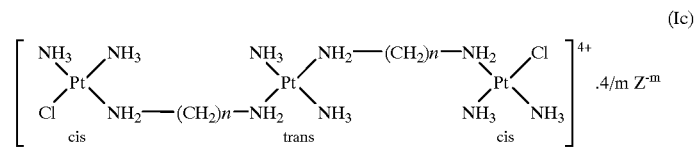

(Ic)

5. Complexes according to claim 1, of formula (Id):

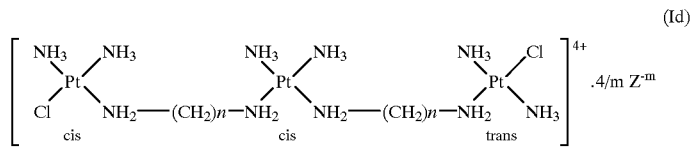
(Id)

6. Complexes according to claim 1, of formula (Ie):

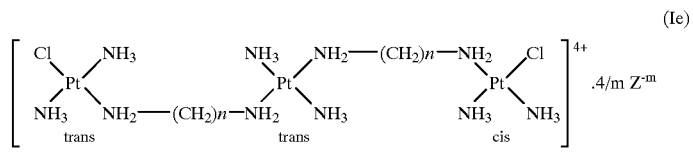
(Ie)

7. Complexes according to claim 1, wherein n is the integer 6.

8. Complexes according to claim 1, wherein $Z^{-m}$ is the chloride or nitrate anion.

9. Pharmaceutical compositions containing one compound according to claim 1 as the active ingredient, in admixture with a suitable carrier.

10. Pharmaceutical compositions wherein a tri-platinum complex of claim 1 is combined with a platinum complex having antitumour activity.

* * * * *